United States Patent [19]
Kim et al.

[11] Patent Number: 5,883,259
[45] Date of Patent: Mar. 16, 1999

[54] BENZOXAZOLE BASED NONLINEAR OPTICAL DERIVATIVES AND POLYMERS OBTAINED THEREFROM

[75] Inventors: Nakjoong Kim; Ki Hong Park, both of Seoul, Rep. of Korea

[73] Assignee: Korea Institute Of Science And Technology, Seoul, Rep. of Korea

[21] Appl. No.: 680,538

[22] Filed: Jul. 9, 1996

[30] Foreign Application Priority Data

Apr. 19, 1996 [KR] Rep. of Korea ................. 1996/11997

[51] Int. Cl.$^6$ ................................ C07D 263/57
[52] U.S. Cl. ................ 548/224; 548/217; 526/260; 526/262; 528/65
[58] Field of Search ............................ 548/224

[56] References Cited

U.S. PATENT DOCUMENTS

| | | | |
|---|---|---|---|
| 3,458,506 | 7/1969 | Bloom et al. | 548/224 |
| 3,822,356 | 7/1974 | Brenneisen et al. | 514/375 |
| 3,985,755 | 10/1976 | Narayanan et al. | 548/217 |
| 3,996,210 | 12/1976 | Fleck et al. | 548/224 |
| 5,216,110 | 6/1993 | Inbaskaran | 528/125 |
| 5,321,084 | 6/1994 | Cross et al. | 525/107 |
| 5,395,846 | 3/1995 | Morris | 514/375 |
| 5,496,826 | 3/1996 | Watson | 514/303 |
| 5,496,853 | 3/1996 | Shiota | 514/469 |
| 5,567,843 | 10/1996 | Lyenko | 548/224 |
| 5,739,344 | 4/1998 | Pews | 548/224 |

FOREIGN PATENT DOCUMENTS 0 360 566 A2  7/1990  European Pat. Off. .

OTHER PUBLICATIONS

Helelyova et al. Chem. Abstr. vol 125 entry 33520, 1996.
Vernigor et al. Chem. Abstr. vol 120 entry 163244, (1993).
Rtischev et al. Chem. Abstr. vol. 110 entry 211942, (1989).
Heleyova et al. Collect Crech Chem Commun. vol. 61 No. 3 pp. 391–380, Mar. 1996.
Burland et al. *Second–Order Nonlinearity in Poled–Polymer Systems*, pp. 31–75, vol. 94 Chem. Review (1994).
Marks et al. *Design, Synthesis, and Properties of Molecule–Based Assemblies with Large Second–Order Optical Nonlinearities*, pp. 155–173, vol. 34 Agnew. Chem. Int. Ed. Engl. (1995).

Miller et al., *Thermally stable chromophore . . .*, SPIE, vol. 2042, 354 (1994).
Mathias et al., *Two–Step Synthesis of Alkyl– and Alkenlbenzoxazole Polymers*, pp. 616–622, Macromolecules (1985) 18.
Robello et al., *Linear Polymers for Nonlinear Optics . . .*, pp. 1–13, J.Polym.Sci., Part A: Polym. Chem., vol. 28, (1990).
Maruyama et al., *Synthesis and Properties of Fluorine–Containing Aromatic Polybenzoxazoles . . .*, pp. 2305–2309, Macromolecules, vol. 21 (1988).
Imai et al. *Polybenzoxazoles and Polybenzothiazoles*, pp. 167–178, Die Makromolekulare Chemie, vol. 83 (1965).
Caruso et al. *Synthesis and Preliminary Characterization of a New Fully Aromatic Mesogenic Polyester Containing a 2–Phenylbenzoxazole Group*, pp. 2290–2293, Macromolecules vol. 25 (1992).
Jen et al. *Thermally Stable Poled Polymers . . .*, pp. 413–420 Mat.Res.Soc.Symp.Proc., vol. 328 (1994).

*Primary Examiner*—Donald G. Daus
*Attorney, Agent, or Firm*—Darby&Darby

[57] ABSTRACT

The present invention provides benzoxazole derivatives and nonlinear optical (NLO) materials obtained therefrom as a novel organic NLO material having following general formula (I), which can be used as optical devices such as electro-optic modulator, optical switch, or the like for treating optical signal in optical communication industry. In order to obtain more stable NLO material, benzoxazole group having high thermal resistance is substituted as a π conjugated unit instead of conventional stilbene or azobenzene group. A variety of NLO materials can be prepared by the synthetic process according to the present invention.

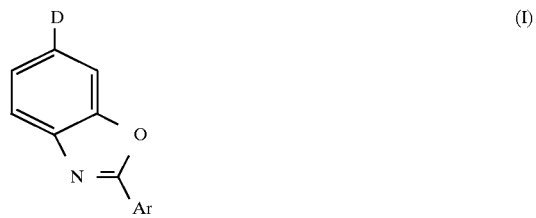

(I)

wherein D and Ar have the same meaning as defined in the aforementioned.

8 Claims, No Drawings

BENZOXAZOLE BASED NONLINEAR OPTICAL DERIVATIVES AND POLYMERS OBTAINED THEREFROM

FIELD OF THE INVENTION

The present invention relates to benzoxazole based nonlinear optical derivatives having excellent thermal stability, and polymers obtained therefrom.

BACKGROUND OF THE INVENTION

Nonlinear Optical (NLO) materials are used as media of second and third harmonic generator and optical devices such as electro-optic modulator, optical switch, or the like for treating optical signal in ultra-high speed optical communication, and are developed as an important element for the forthcoming information age.

The NLO materials can be divided into two groups of inorganic and organic NLO materials. As conventional inorganic NLO materials, $LiNbO_3$ or GaAs crystals may be mentioned. Organic NLO materials, as described in Chemical Review vol.94, No.1, 31–76(1994) published by American Chemical Society, can make materials having higher electro-optic coefficient than that of inorganic NLO materials. In particular, they can be advantageously used in high-speed electro-optic modulator due to their low dielectric constant. Among them, non-crystalline organic NLO polymers have excellent optical properties and processibility so that optical devices may be prepared in low cost.

Organic compounds exhibiting NLO characteristics generally have a structure of electron donor—π conjugatedunit—electron acceptor. In other words, a molecular structure having an electron donor (e.g. nitrogen, oxygen, sulfur) at one end, an electron acceptor (e.g. nitro group, cyano group, sulfone group, or the like) at the other end, and a long π conjugation between them exhibits high optical nonlinearity. Thus, most of the organic compounds showing NLO characteristics as mentioned above are π conjugation type compounds containing stilbene or azobenzene group. Representative examples are dyes such as 4-dimethylamino-4'-nitrostilbene (DANS), 4-[N-ethyl-N-(2- hydroxyethyl)]amino-4'-nitroazobenzene (Disperse Red 1), or the like. These dyes have been frequently used in the field of organic NLO materials because they can be simply synthesized, however, they have thermally weak double bonded π conjugation.

In the field of organic nonlinear optics, various molecular designs have been sought in order to prepare more effective and stable NLO materials [cf. Angew. Chem. Int. Ed. Engl. vol.34, 155–173 (1995)]. For example, a development of novel NLO dye having higher dipole moment(p) and second-order hyperpolarization (β; a process of cross-linking after electric field arrangement (poling) in order to minimize the relaxation of dipolar vector of NLO dye directed to one direction; and introduction of polymer matrix having high glass transition temperature have been attempted. In particular, intensive studies have been recently performed in order to improve thermal stability of organic NLO polymers, which is relatively lower than that of inorganic NLO materials.

In addition, the thermal resistance of dye itself having substantial NLO properties as well as that of polymer matrix have been accounted very much, as described in SPIE, vol.2042, 354–365(1994). In other words, a novel NLO dye which is stable at high temperature is requested in order to minimize thermal decomposition of dye under the poling condition and environment of manufacturing devices and operation at high temperature, and maximize the NLO properties.

The present inventors have noticed a design of a novel NLO material derived from polybenzoxazole which is well known as an aromatic polymer having high thermal resistance and high anti-oxidation stability [cf. Macromolecules, vol.18, 616 (1985)], and developed a novel NLO material having enhanced thermal resistance as compared to conventional NLO materials comprising stilbene or azobenzene group, by substituting the π conjugation of basic skeleton of NLO dye with an aromatic benzoxazole group having more excellent thermal resistance, instead of conventional stilbene or azobenzene.

SUMMARY OF THE INVENTION

The first object of the present invention is to provide benzoxazole based NLO derivatives represented by following formula (I):

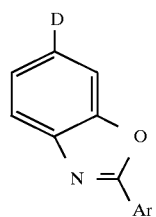

(I)

wherein, D is electron donor such as $NR_1R_2$ or $X_1R_3$ (in the formulas, $R_1$, $R_2$ and $R_3$ independently represents hydrogen, alkyl, hydroxyalkyl, alkyl moiety, aryl or aryl moiety, and $X_1$ is oxygen or sulfur); and Ar is an aromatic group represented by following formula;

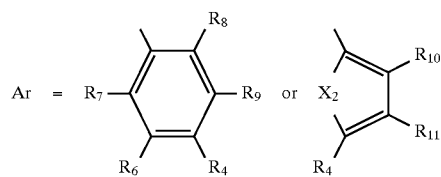

wherein, $R_4$ is hydrogen or an electron acceptor such as nitro, cyano, dicyanovinyl, tricyanovinyl or $SO_2R_5$; $R_5$ is an alkyl, fluoroalkyl or aryl group; $R_6$, $R_7$, $R_8$, $R_9$, $R_{10}$ and $R_{11}$ independently represents hydrogen, hydroxy, halogen, alkyl, aryl, alkoxy, aryloxy or an electron acceptor; $X_2$ is sulfur, oxygen or $NR_{12}$ ($R_{12}$ represents hydrogen, alkyl, hydroxyalkyl, alkyl moiety, aryl or aryl moiety).

Another object of the present invention is to provide a process for preparation of the benzoxazole based NLO derivatives comprising the steps of condensing an aminophenol of the following formula with an aldehyde of the following formula to obtain an hydroxyimine and then oxidizing the hydroxyimine compound.

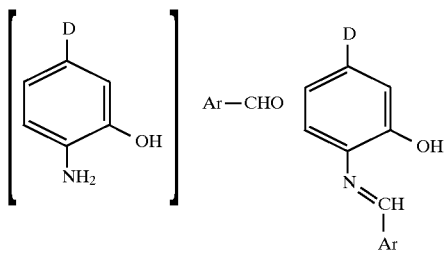

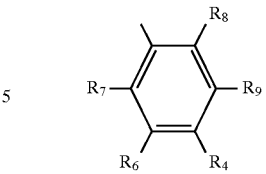

wherein, $R_1$, $R_2$, $R_4$, $R_6$, $R_7$, $R_8$ and $R_9$ are defined as above, may be preferably used.

The derivatives wherein D is $NR_1R_2$ and Ar is an aromatic group of the following formula:

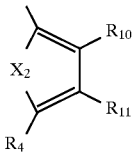

wherein, $R_2$, $R_2$, $R_4$, $R_{10}$, $R_{11}$ and $X_2$ are defined as above, may be also preferably used.

In the formula, D and Ar are defined as above.

Another object of the present invention is to provide a vinyl monomer of the benzoxazole based NLO derivatives according to the present invention.

A still another object of the present invention is to provide a NLO polymer comprising the benzoxazole based NLO derivatives according to the present invention or the vinyl monomer of the benzoxazole based NLO derivatives as its constituents.

DETAILED DESCRIPTION OF THE INVENTION

Here-in-after, the present invention is described in more detail.

The present invention consists of benzoxazole based NLO derivatives, synthesis of vinyl monomers from these derivatives, and synthesis of NLO polymer from these derivatives or monomers.

(1) Benzoxazole based NLO derivatives

The benzoxazole based NLO derivatives represented by the general formula as above have excellent thermal resistance as they comprise an aromatic benzoxazole group instead of conventional stilbene or azobenzene group as π conjugated unit of the basic skeleton.

In the benzoxazole based NLO derivatives according to the present invention, D of the above formula is an electron donor such as $NR_1R_2$ or $X_1R_3$ (in the formulas, $R_1$, $R_2$ and $R_3$ independently represents hydrogen, alkyl, hydroxyalkyl, alkyl moiety, aryl or aryl moiety, and $X_1$ is oxygen or sulfur); and Ar is an aromatic group represented by following formula;

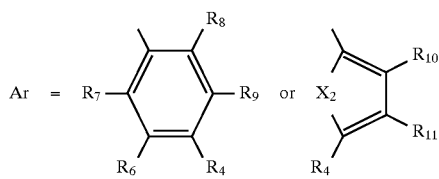

wherein, $R_4$ is hydrogen or an electron acceptor such as nitro, cyano, dicyanovinyl, tricyanovinyl or $SO_2R_5$; $R_5$ is an alkyl, fluoroalkyl or aryl group; $R_6$, $R_7$, $R_8$, $R_9$, $R_{10}$ and $R_{11}$ independently represents hydrogen, hydroxy, halogen, alkyl, aryl, alkoxy, aryloxy or an electron acceptor; $X_2$ is sulfur, oxygen or $NR_{12}$ ($R_{12}$ represents hydrogen, alkyl, hydroxyalkyl, alkyl moiety, aryl or aryl moiety).

Among the benzoxazole based NLO derivatives represented by the above formula, compounds wherein D is $NR_1R_2$ and Ar is an aromatic group of the following formula:

As benzoxazole based NLO derivatives according to the present invention, compounds wherein D is $X_1R_3$ in which $X_1$ is sulfur and $R_3$ is hydrogen, alkyl, hydroxyalkyl, aryl, alkyl moiety or alkylaryl moiety may be preferably used.

As benzoxazole based NLO derivatives according to the present invention, compounds wherein D is $X_1R_3$ in which $X_1$ is oxygen and $R_3$ is hydrogen, alkyl, hydroxyalkyl, aryl, alkyl moiety or alkylaryl moiety may be preferably used.

As an alkyl group described in the definition of the substituent of the present invention, an alkyl group of $C_nH_{2n+1}$ (n=1–10) such as methyl, ethyl, propyl and butyl may be mentioned.

As an aryl group, phenyl group may be mentioned.

As a hydroxyalkyl group, 2-hydroxyethyl group may be mentioned.

As an alkyl moiety, branched or straight chain with substituents comprising from 1 to 10 carbon atoms (e.g., perfluorobutyl) may be mentioned.

As an aryl moiety, one ring or a fused ring with substituents comprising from 5 to 15 carbon or heteroatoms (e.g., 3-hydroxyphenyl) may be mentioned.

The term "halo" used in the present invention represents fluoro, chloro, bromo or iodo.

(2) Synthesis of the benzoxazole based NLO derivatives

In general, conventional stilbene dyes are synthesized by Wittig reaction or Knoevenagel reaction, and azobenzene dyes are synthesized by diazo coupling reaction [J. Polym. Sci: Part A: Polym. Chem., vol.28, 1–13(1990)].

On the other hand, benzoxazole compounds are generally prepared by a two-step reaction comprising of condensation of aminophenol with acid chloride to form a hydroxyamide, and dehydration thereof at high temperature [Macromolecules, vol.21, 2305–2309 (1988)]; or a one-step reaction comprising of dehydration of aminophenol and acid in the presence of condensing agent such as polyphosphoric acid at high temperature [Macromol. Chem.,vol.83, 167–178 (1965)].

The benzoxazole based NLO derivatives of the present invention is prepared by a two-step reaction comprising of condensing aminophenol with aldehyde to prepare hydroxyimine, and oxidizing thereof [Macromolecules, vol.25, 2290–2293 (1988)]. The steps are all performed at room temperature and no side-reaction occurs to produce the product in high yield.

Thus, the process for preparation of the benzoxazole based NLO derivatives according to the present invention comprises steps of condensing an aminophenol compound with an aldehyde compound to obtain hydroxyimine compound, and oxidizing the hydroxyimine. The process has an advantage in that design and modification of the molecular structure may be easily varied, which is an important advantage of organic NLO materials.

The synthesis of the NLO derivatives according to the present invention can be simply represented as follows:

nol compounds and aldehyde compounds, different from the synthesis of conventional NLO derivatives comprising stilbene and azobenzene. The chemical modification of molecular structure can be easily performed, which is an important advantage of organic NLO materials. For example, in case of a NLO derivative comprising hydroxy group in Example 2 below, the dipolar relaxation of organic NLO material can be effectively overcome by using a cross-linking agent having two or more functional groups which can react with these hydroxy groups as described in U.S. Pat. No. 5,321,084. In addition, NLO derivatives comprising thiophene having high second-order hyperpolarizability as described in Mat. Res. Soc. Symp. Proc., vol.328, 413–420 (1994), can be easily synthesized according to the present invention.

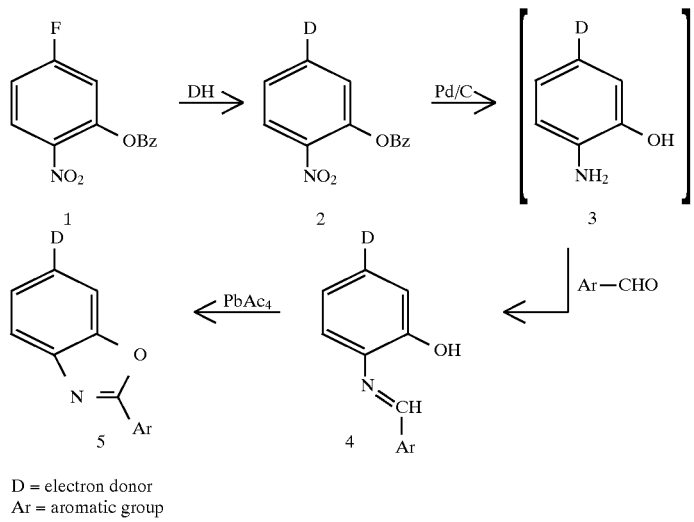

D = electron donor
Ar = aromatic group

To summarize the above reaction formulas, 2-benzyloxy-4-fluoronitrobenzene (compound 1) in which an hydroxyl group had been substituted with a protective benzyloxy group was reacted with a secondary amine, alcohol or thiol derivative to synthesize benzyloxynitro compound (2). Depending upon the nucleophilic compound used in this synthetic step, various electron donor substituents may be synthesized. As described in European Patent Application No. 0,360,566, compound (2) is dissolved in a solvent and reduced using a palladium catalyst under hydrogen atmosphere to quantitatively convert the nitro group to amino group, and benzyloxy group to hydroxy group, respectively, whereby aminophenol compound (3) is synthesized. As the reaction proceeds quantitatively, it is advantageous in view of the yield that the obtained compound 3 is used in situ for the next step without further purification.

To the reaction mixture of the aminophenol compound, corresponding aldehyde compound is added and reacted at room temperature to synthesize compound (4) in high yield. Depending upon the aromatic aldehyde compound used in this synthetic step, new NLO dyes with various electron accepting substituents may be synthesized. After separating and purifying, compound (4) is dissolved in a solvent and oxidized by using lead tetraacetate at room temperature as described in Macromolecules, vol.25, 2290–2293 (1988), to give benzoxazole based NLO derivative (5) of the present invention.

As described above, a variety of novel NLO derivatives with different substituents can be synthesized in high yield because the benzoxazole based NLO derivatives according to the present invention are synthesized by using aminophe- (3) Benzoxazole vinyl monomers $$I-R_{13}-V$$

In the formula, I is defined as above, $R_{13}$ is an alkyl or phenyl; and V is a vinyl moiety represented by following formula:

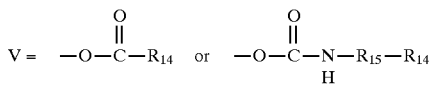

wherein, 4 is $—C(R_{16})=CH_2$; $R_{15}$ is $—C(CH_3)_2C_6H_4—$; $R_{16}$ is hydrogen or methyl group.

The benzoxazole vinyl monomer according to the present invention can be obtained from a compound in which $R_2$ or $R_3$ of the general formula of the benzoxazole based NLO derivative as mentioned above is hydroxyalkyl or hydroxyphenyl. The compound is subjected to a condensation or addition reaction with methylmethacroyl chloride or m-isopropenyl-α,α-dimethylbenzy-lisocyanate, respectively, to synthesize the benzoxazole vinyl monomer.

(4) Benzoxazole based NLO polymer

The present invention provides a polymer represented by following formula from the benzoxazole based NLO derivative represented by the above-described general formula.

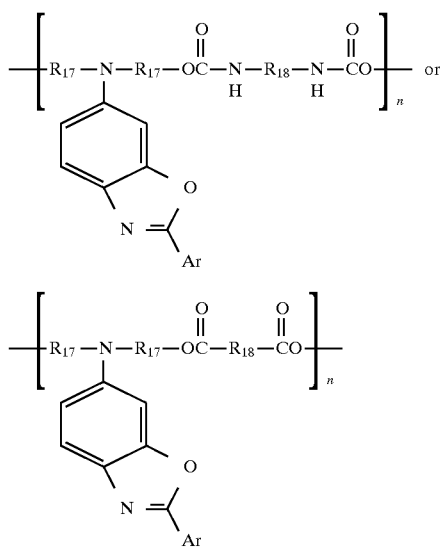

In the formula, $R_{17}$ is alkyl or phenyl; Ar is defined as above; and $R_{18}$ is an aromatic group represented by following formulas;

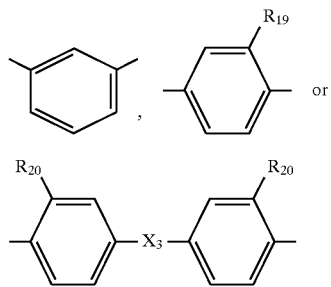

wherein, $R_{19}$ and $R_{20}$ is hydrogen, methyl or methoxy; and $X_3$ is methylene, ether or sulfone.

The benzoxazole polymer represented by the above formulas can be obtained from the compound in which $R_2$ and $R_3$ of the general formula of the benzoxazole based NLO derivatives mentioned above are hydroxyalkyl or hydroxyphenyl group. In other words, the diol compounds are polymerized by a polycondensation or polyaddition with diisocyanate or diacid chloride, respectively, to synthesize the benzoxazole based NLO polymer.

Further, the present invention provides benzoxazole based NLO polymers represented by the following formula:

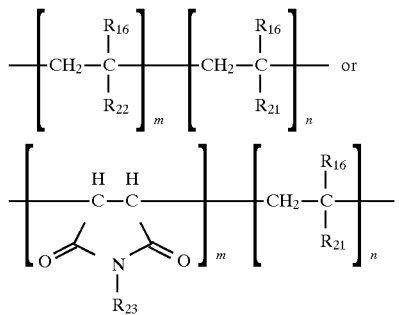

wherein, , is —$COOR_{13}R$ or —$R_{15}NHCOOR_{13}R$, $R_{22}$ is —$COOCH_3$, phenyl, glycidyl or carbazole, and $R_{23}$ is hydrogen, methyl or phenyl (in the formulas, R, $R_{13}$, $R_{15}$ and $R_{16}$ is defined as above); from the benzoxazole based NLO vinyl monomers having the general formula described above.

The benzoxazole polymers represented by above formula can be obtained by radical polymerization or ionic polymerization of the benzoxazole based NLO vinyl monomer having the general formula shown above. Copolymers may be obtained by using benzoxazole based vinyl monomer with a comonomer. As a preferable comonomer, methyl methacrylate, styrene, glycidyl methacrylate, N-vinylcarbazole and N-substituted maleimide may be mentioned.

EXAMPLES

Here-in-after, the present invention will be described in more detail with reference to the Examples, however, it should be noted that the present invention is not restricted to these Examples.

Examples 1 to 4 are synthetic examples of hydroxyimine dyes and benzoxazole based NLO dyes obtained therefrom according to the present invention. The structure of all compounds have been examined by elemental analysis, IR and $^1$H-NMR spectroscopy (200 MHz). The results of analysis of the hydroxyimine dyes and benzoxazole based NLO derivatives synthesized in Examples 1 to 4 are shown in Table 1 and Table 2, respectively.

EXAMPLE 1

2-(4-Nitrophenyl)-6[N-methyl-N-(2-hydroxy-ethyl) amino] benzoxazole

In a 1 liter flask, 37.04 g(0.15 mol) of 2-benzyloxy-4-fluoronitrobenzene (compound 1) and 22.34 g(0.3 mol) of 2-(methylamino) ethanol was dissolved in 400 ml of N,N-dimethyl-formamide (DMF). Potassium carbonate (20.72 g, 0.15 mol) was added thereto, and the mixture was heated with stirring at 100° C. for 12 hours. After cooling to room temperature, the mixture was poured dropwise into 2 liters of water with stirring to precipitate yellow crystalline powder. The precipitation was filtered, washed with water and dried under vacuum. The yellow powder was dissolved in ethanol, reprecipitated in hexane, and then filtered and dried to obtain N-methyl-N-(2-hydroxyethyl)-N-(3-benzyloxy-4-nitro)aniline [yield: 43.1 g, 95%].

m.p. 104°–106° C.

$^1$H-NMR (DMSO-$d_6$): δ3.04(s,3H,NCH$_3$), 3.52(s,4H, CH$_2$), 4.79(s,1H,OH), 5.28(s,2H,OCH$_2$), 6.35–6.41(m, 2H,ArH), 7.31–7.52(m,5H,ArH), 7.89(d,1H,ArH).

Elemental analysis: $C_{16}H_{18}N_2O_4$ (302.33)

calculated: C,63.57% /H,6.00% /N,9.27% found: C,63.5% /H,6.09% /N,9.21%

N-Methyl-N-(2-hydroxyethyl)-N-(3-benzyloxy-4-nitro) aniline (9.07 g, 0.03 mol) synthesized from the above step was dissolved in 200 ml of DMF, and 1 g of 10% palladium/ active carbon dispersed in 10 ml of DMF was added thereto. The mixture was reacted with vigorous stirring under hydrogen atmosphere at room temperature for 1 day. After the reduction, the atmosphere was substituted with nitrogen, and 4-nitrobenzaldehyde (4.53 g, 0.03 mol) was added thereto and reacted for 2 hours at room temperature. The reaction mixture was filtered to remove the catalyst and carbon, and the filtrate was poured into 1 liter of water to precipitate black crystals. The crystals were filtered, washed several times with water, and dried at 80° C. under vacuum. Hydroxyimine compound was obtained as black crystals after recrystallization from a mixed solvent of tetrahydrofuran (THF) and hexane, and drying under vacuum [yield: 7.76 g, 82%].

Elemental analysis: $C_{16}H_{17}N_3O_4$ (315.33)
calculated: C,60.94% /H,5.43% /N,13.33%
found: C,60.9% /H,5.49% /N,13.4%

The hydroxyimine compound (6.31 g, 0.02 mol) synthesized from the above step was dissolved in 300 ml of THF, and 9.35 g of lead tetraacetate (95%) was slowly added thereto with stirring. The reaction mixture was vigorously stirred for 2 hours, and lead diacetate crystals produced as a by-product was removed by filtration. After recrystallization from THF, 2-(4-nitrophenyl)-6-[N-methyl-N-(2-hydroxyethyl)amino]benzoxazole was obtained as dark red crystals [yield: 5.31 g, 85%].

Elemental analysis: $C_{16}H_{18}N_2O_4$ (312.32)
calculated: C,61.34% /H,4.83% /N,13.41%
found: C,61.2% /H,4.85% /N,13.3%

EXAMPLE 2

2-(3-hydroxy-4-nitrophenyl)-6-[N-methyl-N-(2-hydroxyethyl) amino]benzoxazole

The hydroxyimine compound was synthesized in accordance with the procedure of Example 1, by using N-methyl-N-(2-hydroxyethyl)-N-(3-benzyloxy-4-nitro)aniline and 3-hydroxy-4-nitrobenzaldehyde [yield: 80%].

Elemental analysis: $C_{16}H_{17}N_3O_5$ (331.33)
calculated: C,58.00% /H,5.17% /N,12.68%
found: C,57.9% /H,5.11% /N,12.7%

The benzoxazole compound was synthesized in accordance with the procedure of Example 1 from the hydroxyimine compound [yield: 82%].

Elemental analysis: $C_{16}H_{15}N_3O_5$ (329.32)
calculated: C,58.36% /H,4.59% /N,12.76%
found: C,58.2% /H,5.02% /N,12.9%

EXAMPLE 3

2-(2-nitrothiophen)-6-[N-methyl-N-(2-hydroxyethyl) amino]benzoxazole

The hydroxyimine compound was synthesized in accordance with the procedure of Example 1, by using N-methyl-N-(2-hydroxyethyl)-N-(3-benzyloxy-4-nitro)aniline and 5-nitro-2-thiophencarboxylaldehyde [yield: 79%].

Elemental analysis: $C_{12}H_{15}N_3O_4S$ (297.33)
calculated: C,48.48% /H,5.09% /N,14.13%
found: C,48.3% /H,5.07% /N,14.1%

The benzoxazole compound was synthesized in accordance with the procedure of Example 1 from the hydroxyimine compound obtained above [yield: 85%].

Elemental analysis: $C_{12}H_{13}N_3O_4S$ (295.32)
calculated: C,48.81% /H,4.44% /N,14.23%
found: C,48.7% /H,4.40% /N,14.4%

EXAMPLE 4

2-(4-nitrophenyl)-6-[N,N-bis(2-hydroxyethyl) amino] benzoxazole

The hydroxyimine compound was synthesized in accordance with the procedure of Example 1, by using N,N-bis(2-hydroxy-ethyl)-N-(3-benzyloxy-4-nitro)aniline and 4-nitro-benzaldehyde [yield: 79%].

Elemental analysis: $C_{17}H_{19}N_3O_5$ (345.36)
calculated: C,59.12% /H,5.55% /N,12.17%
found: C,59.0% /H,5.61% /N,12.2%

The benzoxazole compound was synthesized in accordance with the procedure of Example 1 from the hydroxyimine compound obtained above [yield: 87%].

Elemental analysis: $C_{17}H_{17}N_3O_5$ (343.34)
calculated: C,59.47% /H,4.99% /N,12.24%
found: C,59.6% /H,5.02% /N,12.1%

TABLE 1

Chemical analysis of hydroxyimine compounds

| Ex. | D,R,X structural formula (m.w.) | m.p. (°C.) | UV[a] $\lambda_{max}$ (nm) | IR[b] (cm$^{-1}$) | $^1$H-NMR(DMSO-d$_6$) (δ) |
|---|---|---|---|---|---|
| 1 | D = NR1R2, R1 = CH3, R2 = CH2CH2OH, R4 = NO2, R6 = R7 = R8 = R9 = H C16H17N3O4 (315.33) | 194–196 | 473 | 1624, 1566 (C=N, C=C) 1505, 1325 (NO2) | 2.94(s, 3H, CH3), 3.34–3.55(m, 4H, CH2), 4.71(t, 1H, OH), 6.20(s, 1H, ArH), 6.26(d, 1H, ArH), 7.36–8.24(m, 5H, ArH), 8.82(s, 1H, =CH), 8.94(s, 1H, ArOH) |
| 2 | D = NR1R2, R1 = CH3, R2 = CH2CH2OH, R4 = NO2, R6 = OH, R7 = R8 = R9 = H C16H17N3O5 (331.33) | 206–208 (dec.) | 496 | 1628, 1568 (C=N, C=C) 1520, 1336 (NO2) | 2.94(s, 3H, CH3), 3.33–3.53(m, 4H, CH2), 4.71 (s, 1H, OH) 6.19–6.25(m, 2H, ArH), 7.34(d, 1H, ArH), 7.61–7.68(m, 2H, ArH), 7.95(d, 1H, ArH), 8.70(s, 1H, =CH), 8.92(s, 1H, ArOH) |
| 3 | D = NR1R2, R1 = CH3, R2 = CH2CH2OH R4 = NO2, R10 = R11 = H | 190–193 (dec.) | 526 | 1626, 1558 (C=N, C=C) 1516, 1322 (NO2) | 2.94(s, 3H, CH3), 3.39–3.58(m, 4H, CH2), 4.72(t, 1H, OH), 6.19–6.29(m, 2H, ArH), |

TABLE 1-continued

Chemical analysis of hydroxyimine compounds

| Ex. | D,R,X structural formula (m.w.) | Hydroxyimine compounds | | | |
|---|---|---|---|---|---|
| | | m.p. (°C.) | UV[a] $\lambda_{max}$ (nm) | IR[b] (cm$^{-1}$) | $^1$H-NMR(DMSO-d$_6$) ($\delta$) |
| | X2 = S<br>C12H15N3O4S<br>(297.33) | | | | 7.26–8.10(m, 3H, ArH),<br>8.95(s, 1H, =CH),<br>9.23(s, 1H, ArOH) |
| 4 | D = NR1R2<br>R1 = R2 = CH2CH2OH,<br>R4 = NO2,<br>R6 = R7 = R8 = R9 = H<br>C17H19N3O5<br>(345.36) | 173–174 | 462 | 1626, 1572<br>(C=N, C=C)<br>1506, 1323<br>(NO2) | 3.41–3.55(m, 8H, CH2),<br>4.77(t, 2H, OH),<br>6.25(d, 2H, ArH),<br>7.36(d, 1H, ArH),<br>8.25(m, 4H, ArH),<br>8.82(s, 1H, =CH),<br>8.93(s, 1H, ArOH) |

[a] measured in CHCl$_3$ solution
[b] KBr pellet

TABLE 2

Chemical analysis of benzoxazole based NLO derivatives

| Ex. | D,R,X structural formula (m.w.) | benzoxazole based NOL derivatives | | | |
|---|---|---|---|---|---|
| | | m.p. (°C.) | UV[a] $\lambda_{max}$ (nm) | IR[b] (cm$^{-1}$) | $^1$H-NMR(DMSO-d$_6$) ($\delta$) |
| 1 | D = NR1R2,<br>R1 = CH3,<br>R2 = CH2CH2OH,<br>R4 = NO2,<br>R6 = R7 = R8 = R9 = H<br>C16H15N3O4<br>(313.32) | 200–203 | 433 | 1630, 1605<br>(C=N, C=C)<br>1508, 1331<br>(NO2) | 2.99(s, 3H, CH3),<br>3.46–3.59(m, 4H, CH2)<br>4.72(t, 1H, OH),<br>6.83(s, 1H, ArH),<br>6.94(d, 1H, ArH),<br>7.56(d, 1H, ArH),<br>8.20–8.35(m, 4H, ArH), |
| 2 | D = NR1R2,<br>R1 = CH3,<br>R2 = CH2CH2OH,<br>R4 = NO2, R6 = OH,<br>R7 = R8 = R9 = H<br>C16H15N3O5<br>(329.32) | 202–204 | 455 | 1614, 1590<br>(C=N, C=C)<br>1504, 1378<br>(NO2) | 2.98(s, 3H, CH3),<br>3.45–3.57(m, 4H, CH2),<br>6.79–6.93(m, 2H, ArH),<br>7.54(d, 2H, ArH),<br>7.72(s, 1H, ArH),<br>7.99(d, 1H, ArH) |
| 3 | D = NR1R2,<br>R1 = CH3,<br>R2 = CH2CH2OH<br>R4 = NO2,<br>R10 = R11 = H,<br>X2 = S<br>C12H13N3O4S<br>(295.32) | 201–203 | 477 | 1623, 1595<br>(C=N, C=C)<br>1508, 1336<br>(NO2) | 2.99(s, 3H, CH3),<br>3.46–3.58(m, 4H, CH2),<br>4.73(s, 2H, OH),<br>6.82–6.93(m, 2H, ArH),<br>7.55(d, 1H, ArH),<br>7.73(d, 1H, ArH)<br>8.16(d, 1H, ArH) |
| 4 | D = NR1R2<br>R1 = R2 = CH2CH2OH,<br>R4 = NO2,<br>R6 = R7 = R8 = R9 = H<br>C17H17N3O5<br>(343.34) | 168–169 | 429 | 1630, 1665<br>(C=N, C=C)<br>1516, 1354<br>(NO2) | 3.49–3.59(m, 8H, CH2)<br>4.79(t, 2H, OH),<br>6.87(q, 1H, ArH)<br>6.99(d, 1H ArH),<br>7.56(d, 1H, ArH),<br>8.23–8.38(m, 4H, ArH) |

[a] measured in CHCl$_3$ solution
[b] KBr pellet

Vinyl monomers were synthesized in accordance with the following procedure (Example 5) by using the benzoxazole dye prepared in Example 1.

EXAMPLE 5

2-(4-nitrophenyl)-6-[N-methyl-N-(methacroylethyl) amino] benzoxazole 2-(4-Nitrophenyl)-6-[N-methyl-N-(2-hydroxyethyl)-amino]benzoxazole (4.73 g, 0.015 mol) prepared in Example 1 was dissolved in 200 ml of dried methylene chloride, and 3.14 g(0.030 mol) of methylmethacroyl chloride was added dropwise thereto with stirring under nitrogen atmosphere at room temperature. Then, after adding triethylamine (2 ml), the mixture was stirred at room temperature for 3 hours and then at 40° C. for 12 hours. After cooling, the solution was extracted with water/methylene chloride, and the organic layer was dried over anhydrous magnesium sulfate. After filtration, the solvent was evaporated to obtain red crystalline powder. The impurities were removed by silica gel column chromatography. The product was finally recrystallized from a mixed solvent of THF and hexane to give red crystals [yield: 4.35 g, 76%].

m.p. 160°–162° C. UV-Vis:λ(CHCl$_3$) 432 nm $^1$H-NMR (DMSQ-d$_6$): δ 3.60–3.74(s,6H,CH$_2$), 4.25(s, 4H,CH$_2$), 7.06–8.31(m,15H,ArH), 9.54(s,2H,NH)

Elemental analysis: C$_{32}$H$_{27}$N$_5$O$_7$ (593.60)

calculated: C,64.75% /H,4.58% /N,11.80% found: C,64.1% /H,4.66% /N,11.4%

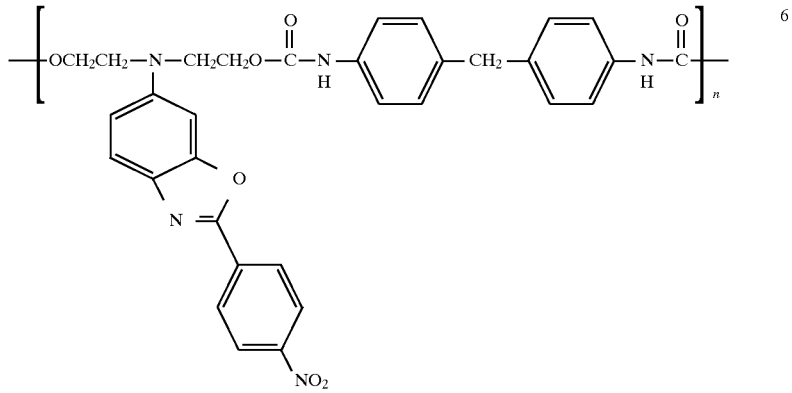

$^1$H-NMR (DMSO-d$_6$): δ 1.79(s,3H,CH$_3$), 3.01(s,3H, NCH$_3$), 3.75(t,2H,CH$_2$),4.29(t,2H,CH$_2$),5.61(s, 1H=CH$_2$),5.93(s,1H,=CH$_2$), 6.89–7.05(m,2H,ArH), 7.60(d,1H,ArH), 8.24–8.38(m, 4H,ArH-NO$_2$).

Elemental analysis: C$_{20}$H$_{19}$N$_3$O$_5$ (381.39)

calculated: C,62.99% /H,5.02% /N,11.02% found: C,62.9% /H,5.04% /N,11.1%

In the following Example 6, polyurethane was synthesized by polyaddition of 2-(4-nitrophenyl)-6-[N,N-bis(2-hydroxyethyl) amino]benzoxazole (benzoxazole diol monomer) prepared in Example 4 and a diisocyanate; and in the following Example 7, copolymer was synthesized by radical copolymerization of 2-(4-nitrophenyl)-6-[N-methyl-N-methacroylethyl)amino]benzoxazole (vinyl monomer) with methyl methacrylate as a representative vinyl comonomer.

EXAMPLE 6

Synthesis of Polyurethane

In a 50 ml flask contained with a magnetic stirrer, 1.036 g(3 mmol) of 2-(4-nitrophenyl)-6-[N,N-bis(2-hydroxyethyl) amino]benzoxazole prepared in Example 4 was charged, and, 8 ml of dried N-methylpyrrolidone (NMP) was added to be dissolved. Methylene diphenylisocyanate (MDI) (0.751 g, 3 mmol) and then dibutyltin dilaurate (0.1 ml) as a polymerization catalyst were added thereto, and the solution was polymerized at 60° C. for 12 hours under nitrogen atmosphere. After polymerization, the polymer solution was poured dropwise into methanol to precipitate the produced polymers. To remove the unreacted monomers, the precipitated polymers were filtered and dissolved again in DMF, and then re-precipitated in methanol. The precipitated red powder was filtered and dried under vacuum to obtain the polymer having the following structure (6) [yield: 1.64 g, 92%].

Glass transition temperature (Tg) measured by differential scanning calorimetry: 145° C.

UV-Vis:λ$_{max}$ (film) 440 nm

IR (KBr pellet): 1715(C=O), 1630 and 1601(C=N, C=C), 1518 and 1325 cm$^{-1}$(NO$_2$)

EXAMPLE 7

Synthesis of Polymethylmethacrylate Copolymer

In a 25 ml pyrex polymerization tube which can be vacuum sealed contained with a magnetic stirrer, 1.907 g(5 mmol) of 2-(4-nitrophenyl)-6-[(N-methacroylethyl-N-methyl)amino]benzoxazole prepared in Example 5 and 0.501 g(5 mmol) of methyl methacrylate as a comonomer were charged, and they are dissolved in dried NMP (15 ml). To the solution, azobisisobutyronitile (AIBN) (0.016 g, 0.1 mmol) was added. The polymerization tube was soaked in liquid nitrogen and completely evacuated by repeating the process of chilling—forming vacuum—thawing. Then the tube was vacuum sealed by using a gas burner. The tube was transferred to an isothermal reaction bath maintained at 65° C. and subjected to polymerization under stirring for 3 days. After polymerization, the polymer solution was poured dropwise into methanol to precipitate the polymers produced. In order to remove the unreacted monomers and oligomers, the precipitated polymers were filtered, dissolved again in 1,1,2,2-tetrachloroethane and re-precipitated in methanol to purify the polymers. The red powdery polymer obtained was dried in-vacuo to yield copolymers having the following structure (7) [yield: 1.8 g, 75%].

Glass transition temperature (Tg) measured by differential scanning calorimetry: 134° C.

UV-Vis:δ$_{max}$ (film) 434 nm

IR (KBr pellet): 1728(C=O), 1631 and 1606(C=N, C=C), 1518 and 1344 cm$^{-1}$(NO$_2$)

1H-NMR (CDCl$_3$): δ0.80–0.98(m,CH$_3$), 1.81(s, CH$_2$), 2.96-(s,NCH$_3$), 3.55(m,CH$_2$OCH$_3$), 4.11(s,CH$_2$), 6.77–8.15(m, ArH).

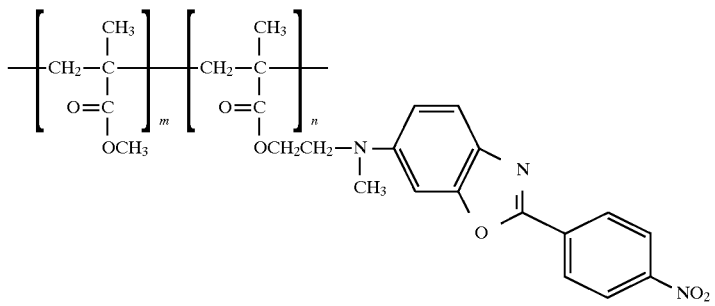

What is claimed is:

1. A benzoxazole based nonlinear optical derivatives represented by the following formula (I):

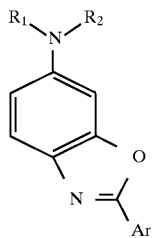

wherein, $R_1$ represents lower alkyl, lower hydroxyalkyl, or phenyl; and $R_2$ represents lower hydroxyalkyl or phenyl;

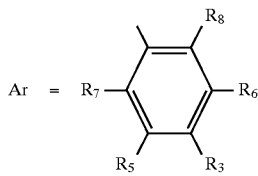

wherein, $R_3$ is nitro, cyano, dicyanovinyl, tricyanovinyl, or $SO_2R_4$ where $R_4$ is a lower alkyl, lower fluoroalkyl or phenyl; $R_5$ and $R_6$ independently represent hydrogen, hydroxy, lower alkyl, halogen, phenyl, lower alkoxy, or phenyloxy; $R_7$ and $R_8$ independently represent hydrogen, hydroxy, halogen, methyl, trifluoromethyl and $O(CH_2)_nCH_3$ wherein n=0–7; and $R_9$ and $R_{10}$ independently represent hydrogen, nitro, cyano, dicyanovinyl or tricyanovinyl.

2. The benzoxazole based nonlinear optical derivatives according to claim 1 wherein $R_1$ is a lower alkyl group; $R_2$ is a lower hydroxyalkyl group; and $R_3$ is a nitro group.

3. The benzoxazole based nonlinear optical derivatives according to claim 1 wherein $R_1$ is a methyl group and $R_2$ is a hydroxyethyl group.

4. The benzoxazole based nonlinear optical derivatives according to claim 1 wherein both $R_1$ and $R_2$ represent a lower hydroxyalkyl group and $R_3$ is a nitro group.

5. The benzoxazole based nonlinear optical derivatives according to claim 4 wherein both $R_1$ and $R_2$ represent a hydroxyethyl group.

6. A compound according to claim 1 wherein the compound is 2-(4-nitrophenyl)-6[N-methyl-N-(2-hydroxyethyl) amino]benzoxazole.

7. A compound according to claim 1 wherein the compound is 2-(3-hydroxy-4-nitrophenyl-6-[N-methyl-N-(2-hydroxyethyl) amino]benzoxazole.

8. A compound according to claim 1 wherein the compound is 2-(4-nitrophenyl)-6-[N,N-bis(2-hydroxyethyl) amino]benzoxazole.

* * * * *